United States Patent [19]

Fukazawa et al.

[11] Patent Number: 5,116,979
[45] Date of Patent: May 26, 1992

[54] DIHYDROCAFFEIC ACID DERIVATIVES AND PHARMACEUTICAL PREPARATIONS CONTAINING SAME

[75] Inventors: Nobuyuki Fukazawa; Hajime Iizuka; Osamu Yano, all of Mobara; Yukio Miyama, Chosei, all of Japan

[73] Assignee: Mitsui Toatsu Chemicals, Incorporated, Tokyo, Japan

[21] Appl. No.: 578,494

[22] Filed: Sep. 6, 1990

[30] Foreign Application Priority Data

Sep. 12, 1989 [JP] Japan .................... 1-234646

[51] Int. Cl.$^5$ .......................... C07D 295/10
[52] U.S. Cl. .................. 544/172; 544/237.5; 544/171; 544/173; 544/174; 544/175; 544/176
[58] Field of Search ............... 544/172, 171, 173, 174, 544/175, 176; 514/237.5

[56] References Cited

U.S. PATENT DOCUMENTS 4,053,509  11/1977  Faro et al. .................... 260/557
4,529,604  7/1985   Kaiser ........................ 514/654

FOREIGN PATENT DOCUMENTS 0101633  2/1984  European Pat. Off. .
0261977  9/1987  European Pat. Off. .
033352   2/1989  European Pat. Off. .
0333522  3/1989  European Pat. Off. .

OTHER PUBLICATIONS

Organic Synthesis, Coll. vol. 3, pp. 575–576, John Wiley & Sons.
Fiat Final Report No. 1313, p. 222 (1948).

Primary Examiner—Marianne Cintins
Assistant Examiner—Jessica H. Nguyen
Attorney, Agent, or Firm—Nixon & Vanderhye

[57] ABSTRACT

Dihydrocaffeic acid derivatives are here disclosed which are applicable as medicines having excellent absorbency in the case of oral administration and good concentration retention in blood.

The disclosed compounds have the function to induce the production and secretion of a nerve growth factor (NGF) in the brain tissue, and therefore they are effective as medicines for the progression inhibition and therapy of regressive disorders of the central nervous system.

7 Claims, No Drawings

DIHYDROCAFFEIC ACID DERIVATIVES AND PHARMACEUTICAL PREPARATIONS CONTAINING SAME

BACKGROUND OF THE INVENTION

1. Field of the Invention

The present invention relates to dihydrocaffeic acid derivatives and use as medicines thereof. More specifically, it relates to dihydrocaffeic acid derivatives having the ability to induce the production and secretion of nerve growth factor (hereinafter abbreviated as "NGF") in the local tissue of the brain, and to prophylactic and therapeutic preparations for regressive disorders of the central nervous system containing these derivatives as active ingredients.

2. Description of the Related Art

Researches have been advanced rapidly in order to establish early diagnosis and etiological therapy for various kinds of senile diseases along with the increasing average span of life in the world. Regressive disorders of the central nervous system are also the principal subjects of researches. In particular, senile dementia of Alzheimer type (hereinafter abbreviated as "SDAT") is getting a serious social problem in that SDAT noticeably increases primarily in advanced countries and in that SDAT is progressive and takes a tragic course. Particularly in recent years, many researchers and clinicians have extensively investigated SDAT, but neither fundamental elucidation of the disease nor effective early diagnosis and therapy have been established.

However, according to many accumulated pathological findings, it has been clarified that direct causes of the decline of memory and disorientation which are characteristic early symptoms of SDAT are the progressive degeneration of magnocellular cholinergic tracts and the insufficiency of its responsible region, the aforesaid cholinergic tracts being projected from the basal forebrain into the cerebral cortex and hippocampus which are the centers of memory and learning. In fact, there is the report that the symptoms of SDAT have been slightly relieved by administering, to SDAT patients, a precursor in acetylcholine biosynthesis or an inhibitor of choline esterase as an activation treatment for the brain cholinergic neuron. However, the results are not considered to be as effective as expected.

NGF has been researched widely since it was discovered by R. Levi-Monterlcini, S. Cohen et al., and it has already been certified by some physiological experiments that NGF is the essential factor for the peripheral nervous system relating to differentiation and growth of sensory and sympathetic nerves of a fetus and relating to the survival and maintenance of functions of the sympathetic neurons of an adult.

NGF is a biologically active substance which is present in ultra trace amounts, and therefore in spite of researches for a long period of time, any precise information has not been obtained which is concerned with the distribution and movement of NGF in the tissue for directly supporting the vital functions thereof. Most recently, a highly sensitive enzyme-linked immunosorbent assay (hereinafter abbreviated as ELISA) to identify the active subunit of NGF, i.e., $\beta$-NGF (hereinafter simply referred to as "NGF") has been developed and improved, so that detection-sensitivity and specificity suitable for the above-mentioned examination have been attained [S. Furukawa et al., J. Neurochem., 40, 734-744 (1983); S. Korshing and H. Thoenen, Proc. Natl. Acad. Sci. USA, 80, 3513-3516 (1983)].

Furthermore, the NGF gene has been cloned and its structure has been analyzed, and a method for determining messenger RNA (hereinafter abbreviated as "mRNA") of $\beta$-NGF has been also established which makes use of complementary DNA (hereinafter abbreviated as "cDNA") as a probe [D. L. Shelton and L. F. Reichardt, Proc. Natl. Acad. Sci. USA, 81, 7951-7955 (1984); and R. Heumann et al., EMBO J., 3, 3183-3189 (1984)].

The utilization of this technique has demonstrated that a positive correlation is present between the degree of sympathetic innervation in the peripheral nervous system and the gene expression of NGF in the innervated tissue.

More surprisingly, NGF has also been detected in the central nervous system of rates, particularly in hippocampus, neocortex, basal forebrain, e.g., septum, olfactory bulb, diagonal band of Broca and nucleus basal magnocellularis. In addition, it has been apparent that the mRNA content of NGF is high in the hippocampus and neocortex, but the content thereof in the septum of the basal forebrain is as low as in other regions of the brain in which no NGF is detected [S. Korshing et al., EMBO J., 4, 1389-1393 (1985)]. Afterward, the results of the experiments have been successively traced by other research groups [D. L. Shelton and L. F. Reichardt, Proc. Natl. Acad. Sci. USA, 83, 2714-2718 (1986); S. R. Whittemore et al., Proc. Natl. Acad. Sci. USA, 83, 817-821 (1986)].

According to these results, the NGF gene is expressed not only in the peripheral nervous system but also in the central nervous system, and moreover it has been elucidated that NGF is produced and secreted in the innervating regions of the cholinergic tracts projecting from the origins of the basal forebrain to the neocortex and hippocampus, i.e., the centers of memory and learning, and it is then taken up at the nerve endings and transported in a retrograde manner through axons to reach somata in the origins. It has been already certified by a series of physiological experiments that NGF is the essential factor for the survival and the maintenance of functions in the cholinergic tracts. Thus, these results have demonstrated that NGF specifically functions as a "neurotropic factor" also in the central nervous system.

Afterward, these experiments have been traced by some research groups and have also been supported by investigations regarding NGF receptors and their distribution in the brain.

In the course of the researches on the function of NGF as the neurotropic factor in the central nervous system, the present inventors have got to know that the disorders of memory and learning which are the early symptoms of SDAT are directly caused by the progressive degeneration of cholinergic tracts and the insufficiency of the responsible region which is brought about thereby, but the truly fundamental cause of the disorders is the insufficiency of the production and secretion of NGF in particular regions of the brain.

That is, the present inventors consider that a conventional symptomatic therapy against SDAT such as a supplementation therapy and/or an availability improvement therapy by the use of acetylcholine cannot provide remarkably good results, and that if the functionally vicious cycle between the responsible nerves and regions under their control can be cut off by maintaining the production and secretion of NGF in the cerebral cortex and hippocampus, more effective results can be obtained.

In this connection, the technique for mass production of human-type β-NGF has already been achieved by the cloning of a gene, but the supplemental therapy of NGF itself which is a protein having a molecular weight of more than 10,000 is considerably limited from pharmacological and pharmaceutical viewpoints. In particular, the application of NGF to the central nervous system is far from realization at this point of time.

In view of the foregoing, it is important to search a low-molecular weight compound having the ability to induce the production and secretion of NGF in the particular tissue so as to establish the substantial and effective supplemental NGF therapy. The present inventors have already reported catechol derivatives having such a function (Ikeda: Japanese Patent Laid-open No. 63-83020 and Japanese Patent Application No. 63-63516). Furthermore, there are also reports from Furukawa et al. [Y. Furukawa et al., J. Boil. Chem., 261, 6039 (1986) and FEBS Letters, 208, 258 (1986)]. These reported compounds are excellent in the production and secretion of NGF, but their absorbency in the case of oral administration and their concentration retention in blood are not sufficient.

SUMMARY OF THE INVENTION

An object of the present invention is to provide a medicine having the ability to induce the production and secretion of NGF in a particular tissue as a substantial and effective supplemental therapy. That is, a compound having an activity to promote, in regions under the control of specific nerves, the production and secretion of NGF which functions as a "neurotropic factor" for the responsible nerves or a modified compound obtained under customary pharmacological and pharmaceutical considerations are expected to increase the feed of NGF into the locus of degenerated nerves and to recover their function, when the compound is dosed in a usual administration manner. In particular, the utilization of the compound is most effective for the treatment of SDAT having the disorders of the central nervous system for which any fundamental therapy has not been established yet. In the early stage of the SDAT symptoms; the peripheral administration of the above-mentioned compound can enhance the ability of the NGF production and secretion in the cerebral cortex and hippocampus regions of the central nervous system in order to inhibit the progress of characteristic degeneration in the responsible cholinergic neurons and to promote the repair of the damaged neurons and reinnervation by the surviving neurons. In short, the present invention intents to provide an epoch-making therapy on the basis of a new functional conception in which the plasticity of the brain is utilized.

Another object of the present invention is to provide a medicine having excellent absorbency in the case of oral administration and good concentration retention in blood and having the ability to induce the production and secretion of NGF.

The compounds of the present invention are various acyl compounds represented by the general formula (I) in which hydroxyl groups of dihydrocaffeic acid are replaced by acyl group, so the transition of medicine to the brain system in these compounds are heightened. Therefore, these compounds are considered to be effective as therapy medicines for the above-mentioned disorders.

The present inventors have searched low-molecular weight compounds having the ability to induce the production and secretion of NGF in specific tissues.

As a result, they have found that specific derivatives of dihydrocaffeic acid have the function to induce the production and secretion of NGF, are effective to inhibit the progression and effective for the therapy of regressive disorders of the central nervous system, and can improve the transition of the medicine to the brain system. The present invention has been completed on the basis of this knowledge.

That is, the present inventions are dihydrocaffeic acid derivatives represented by the general formula (I)

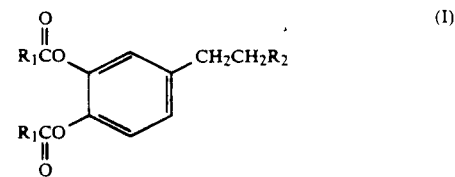

(wherein $R_1$ is an alkyl group having 2 or more carbon atoms, an aryl group, a substituted aryl group, a heteroaryl group or a substituted aryl group; $R_2$ is

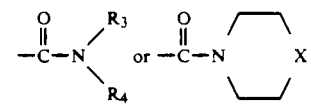

wherein each of $R_3$ and $R_4$ is independently a hydrogen atom, alkyl group, cycloalkyl group, adamantyl group, aryl group or substituted aryl group, and X is a direct bond, a methylene group, oxygen atom or NH group, proviso that $R_3$ and $R_4$ both must not be simultaneously hydrogen atoms or alkyl groups having 3 or less carbon atoms), salts of these derivatives, and a medicine which are effective to inhibit the progression and effective for the therapy of regressive disorders of the central nervous system.

DETAILED DESCRIPTION OF THE INVENTION

In the dihydrocaffeic acid derivatives represented by the general formula (I), examples of the alkyl group having 2 or more carbon atoms of $R_1$ include straight-chain alkyl groups such as an ethyl group, propyl group, butyl group, hexyl group, octyl group, decyl group, lauryl group, hexadecyl group and stearyl group and branched alkyl groups such as an isopropyl group and isobutyl group; examples of the aryl group include a phenyl group and naphthyl group; examples of the substituted aryl group include a benzyl group, phenethyl group and p-methylphenyl group; examples of the heteroaryl group include a pyridyl group, pyrimidyl group, imidazolyl group and furyl group; and examples of the substituted heteroaryl group include halogen-substituted pyridyl group, methylpyridyl group and methylimidazolyl group. Furthermore, examples of the alkyl group of $R_3$ and $R_4$ include the above-mentioned alkyl groups each having two or more carbon atoms and methyl group; and examples of the cycloalkyl group include a cyclopropyl group, cyclobutyl group, cyclopentyl group, cyclohexyl group and cycloheptyl group. Moreover, typical examples of the

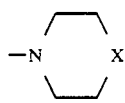

of $R_2$ in the general formula (I) include a pyrrolidino group, piperidino group, morpholino group and piperazino group.

Next, reference will be made to the preparation procedure of the compound according to the present invention.

The first preparation procedure comprises subjecting a compound represented by the general formula (II) and a corresponding acid halide or acid anhydride to a usual esterification reaction in order to obtain a compound represented by the general formula (I)

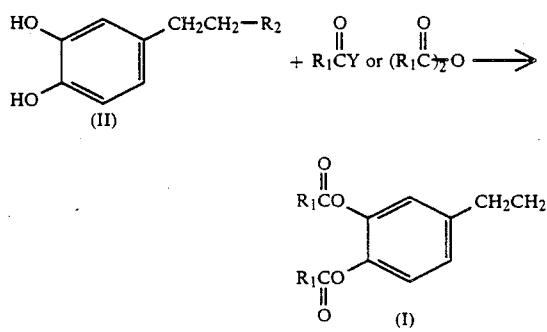

(wherein $R_1$ and $R_2$ are as defined above, and Y is a chlorine atom or bromine atom).

The above-mentioned esterification reaction is carried out in a solvent such as benzene, toluene, chloroform, tetrahydrofuran or dimethylformamide in the presence of a base such as pyridine, triethylamine or sodium hydroxide at a reaction temperature of from 0° to 50° C. However, the compound represented by the general formula (II) can be synthesized by thermally condensing a commercially available ethyl dihydrocaffeate and a corresponding amine.

Here, "thermally" means that heating is carried out at a temperature in the range of from room temperature to 200° C. In most cases, the above-mentioned reaction proceeds in the absence of any solvent, but in some cases, an excess amount of a corresponding amine or an inert solvent such as toluene or xylene may be used.

Next, the second preparation procedure of the compound according to the present invention comprises the steps of esterifying dihydrocaffeic acid and a corresponding acid halide or an acid anhydride, forming a corresponding acid chloride by the use of thionyl chloride, and then reacting the acid chloride with a corresponding amine in the presence of a base

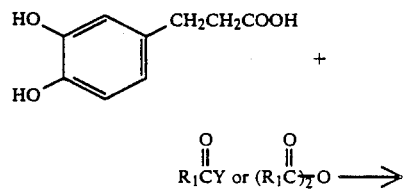

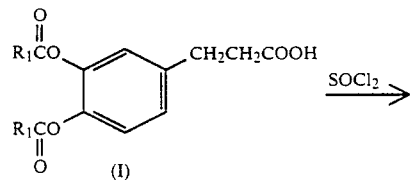

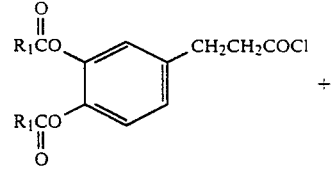

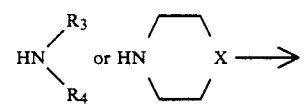

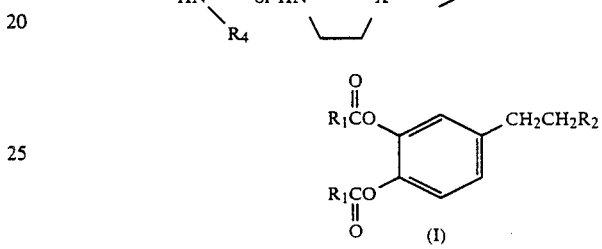

(wherein $R_1$, $R_2$, $R_3$, $R_4$, X and Y are as defined above).

In this case, the above-mentioned base is an organic base such as pyridine or triethylamine, an inorganic base such as sodium hydroxide or potassium hydroxide, or an excess amount of a corresponding amine. The reaction temperature is preferably in the range of from 0° to 50° C. The solvent is preferably the above-mentioned organic base, water, or an organic solvent such as chloroform, tetrahydrofuran or benzene. Alternatively, the diacyl compound of dihdyrocaffeic acid which is obtained herein and a corresponding amine may be subjected to a usual condensation reaction by the use of such a condensation agent (e.g., dicyclohexylcarbodiimide) as used in a usual peptide synthesis chemistry.

Next, the following tests were carried out to confirm the effectiveness of the compound according to the present invention to the progress inhibition and the therapy of regressive disorders of the central nervous system.

That is, NGF was produced and secreted in a culture medium containing the compound of the present invention by the use of a mouse fibroblast cell line, L-M cells (ATCC, CCLI, 2) which had been reported by Furukawa [Y. Furukawa et al., J. Biol. Chem., 261, 6039 (1986)], and the concentration of the thus produced NGF was then measured by the highly sensitive ELISA method.

Furthermore, the concentration of NGF was also measured in a system using astroglial cells which were considered as the major source for the production and secretion of NGF in the central nervous system. It was clarified from the results of these tests that the compounds of the present invention had an extremely high ability to promote the production and secretion of NGF. As a result, it has been confirmed that the compounds of the present invention can become preventive and therapeutic preparations effective for the regressive disorders in the central nervous system, particularly for SDAT.

In addition, compared to the dehydrocaffeic acid, the compounds of the present invention have various acyl groups instead of hydroxyl group, therefore they are excellent in absorbency in the case of oral administration, concentration retention in blood and enhancement of NGF concentration in the brain according to in vivo tests, and have a low acute toxicity. Thus, the compounds of the present invention have many advantages as a medicine, in contrast to compounds in which the hydroxy groups remain.

When each compound of the present invention is used as the preventive or therapeutic pharmaceutical agent for the regressive disorders of the central nervous system, the dose and formulation of the compound depend naturally upon physical properties of the compound, symptoms of the patient and the other factors. In the case of oral administration, the does of the compound for an adult is from 50 to 1000 mg a day, and the compound can be given in a single dose or in divided doses in the form of tablets, granules, powder, suspension or capsules. In the case of non-oral administration, 1 to 100 mg of the compound can be given in a single dose or in divided doses in the form of injections, suppositories or isotonic solutions for infusion.

For example, in preparing the tablets, crystalline cellulose, light anhydrous silicic acid or the like can be used as an adsorbent, and corn starch, lactose, calcium phosphate, magnesium stearate or the like can be used as an excipient. Moreover, in preparing the injection, the compound of the present invention can be used in the state of an aqueous solution, an aqueous suspension of cotton seed oil, corn oil, peanut oil, olive oil or the like, or an emulsion obtained by using a surface active agent such as HCO-60.

Now, the present invention will be described in more detail with respect to the following examples, but these examples are not to be construed as limiting the scope of the invention.

EXAMPLE 1

N-[3-(3,4-Dinicotinoyloxyphenyl)-propionyl]morpholine (a) 3 g of dihydrocaffeic acid and 1.43 g of morpholine were dissolved in 20 ml of DMF (dimethylformamide), and 202 mg of DMAP (dimethylaminopyridine) and 3.4 g of DCC (dicyclohexylcarbodiimide) were further added thereto under cooling, followed by allowing the mixture to stand overnight. The deposited dicyclohexyl urea was removed therefrom by filtration, and the resultant filtrate was then distilled off under reduced pressure. Afterward, the residue was washed with ether in order to obtain 3.8 g of N-[3-(3,4-dihydroxyphenyl)propionyl]morpholine in the state of light yellow crystals having a melting point of from 211° to 213° C.

(a)' 3 g of ethyl dihydrocaffeate was mixed with 3 g of morpholine, and the mixture was then heated with stirring at 150° C. for 2 hours. After cooling, the reaction solution was concentrated, and the resultant residue was then purified through a silica gel column chromatography. Elution was then carried out with a mixture of chloroform:methanol=20:1, thereby obtaining 3.7 g of N-[3-(3,4-dihydroxyphenyl)propionyl]morpholine having a melting point of from 211° to 213° C.

(b) In 100 ml of chloroform was suspended 2.51 g of N-[3-(3,4-dihydroxyphenyl)propionyl]morpholine obtained in the preceding paragraph (a) or (a)', and 3.56 g of nicotinic acid chloride hydrochloride was further added thereto under cooling. Afterward, 5.6 ml of triethylamine was gradually added to the reaction solution, followed by stirring at room temperature for 4 hours. The reaction solution was washed with a saturated saline solution and then dried over Glauber's salt, and the solvent was distilled off under reduced pressure. The resultant residue was purified through a silica gel column chromatography. Elution was then carried out with a mixture of chloroform:methanol=30:1, thereby obtaining 1.99 g of N-[3-(3,4-dinicotinolyloxyphenyl)-propionyl]morpholine.

EXAMPLE 2

N-[3-(3,4-Dibenzoyloxyphenyl)propionyl]morpholine (a) 3 g of dihydrocaffeic acid was dissolved in 20 ml of pyridine, and 5 g of benzoyl chloride was then gradually added thereto under cooling. After stirring at room temperature for 2 hours, the solvent was distilled off, and the resultant residue was then poured into 50 ml of ice water. This solution was neutralized with 6N hydrochloric acid and then extracted with 50 ml of chloroform twice. After washed with a saturated saline solution, the extracted material was dried over Glauber's salt, and the solvent was then distilled off under reduced pressure, thereby obtaining 6.8 g of 3-(3,4-dibenzoyloxyphenyl)propionic acid.

(b) 6 g of 3-(3,4-dibenzoyloxyphenyl)propionic acid was dissolved in 20 ml of benzene, and 2 g of thionyl chloride was added thereto. After stirring at 60° C. for 2 hours, the solvent was distilled off in order to obtain crude 3-(3,4-dibenzoyloxyphenyl)propionic acid chloride. To 50 ml of chloroform was added 2.8 g of morpholine, and the above-mentioned acid chloride was then slowly added dropwise thereto under cooling. After stirring at room temperature for 2 hours, the reaction solution was washed with a saturated saline solution and then dried over Glauber's salt, and the solvent was then distilled off under reduced pressure. The resultant residue was purified through a silica gel column chromatography. On eluting with ethyl acetate, 6.7 g of N-[3-(3,4-dibenzoyloxyphenyl)propionyl]morpholine was obtained.

EXAMPLES 3 to 20

The same reaction and treatment as in Example 1 or 2 were effected in order to obtain compounds of Examples 3 to 20, as shown in Table 1.

TABLE 1

Compound of the present invention

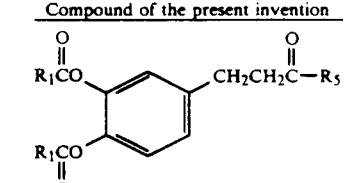

| Example | Structure |   | m.p. (°C.) |
|---|---|---|---|
|   | $R_1$ | $R_5$ |   |
| 1 | 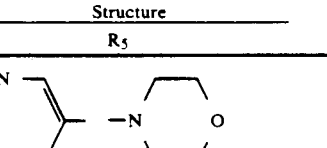 |   | Oily |

TABLE 1-continued

Compound of the present invention

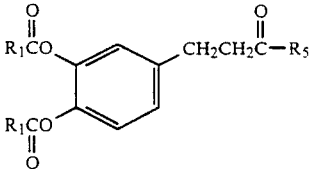

| | R₁ | R₅ | mp |
|---|---|---|---|
| 2 | 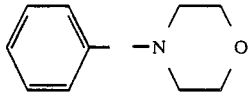 | 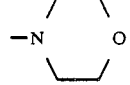 | 123–125 |
| 3 | (CH₃)₃C— | 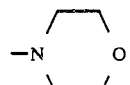 | Oily |
| 4 | CH₃(CH₂)₂— | 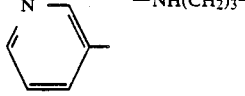 | Oily |
| 5 | 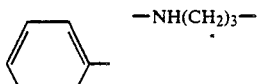 | —NH(CH₂)₃—CH₃ | 104–106 |
| 6 | 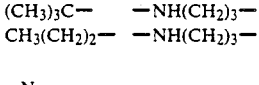 | —NH(CH₂)₃—CH₃ | 100–102 |
| 7 | (CH₃)₃C— | —NH(CH₂)₃—CH₃ | Oily |
| 8 | CH₃(CH₂)₂— | —NH(CH₂)₃—CH₃ | Oily |
| 9 | 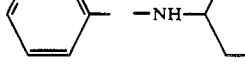 | —NH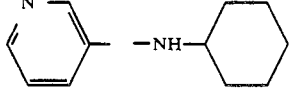 | 139–146 |
| 10 | 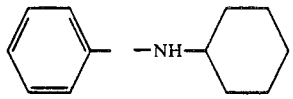 | —NH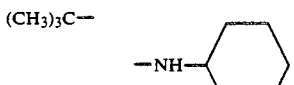 | 133–136 |
| 11 | (CH₃)₃C— | —NH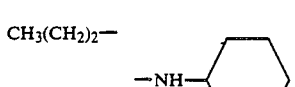 | 66–69 |
| 12 | CH₃(CH₂)₂— | —NH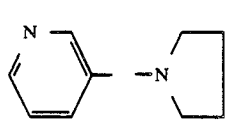 | 100–102 |
| 13 |  | —N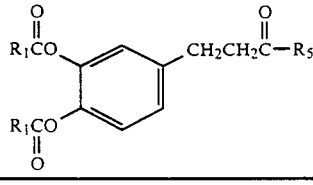 | Oily |
| 14 | 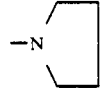 | —N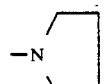 | 129–131 |
| 15 | (CH₃)₃C— | —N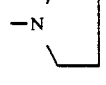 | Oily |
| 16 | CH₃(CH₂)₂— | —N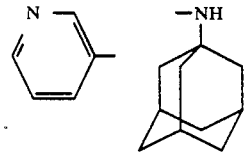 | 64–66 |
| 17 | 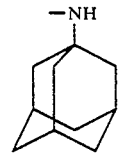 | —NH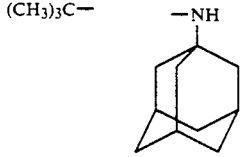 | Amorphous powder |
| 18 | 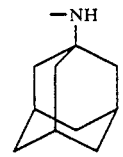 | —NH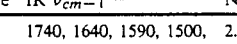 | Amorphous powder |
| 19 | (CH₃)₃C— | —NH | Amorphous powder |
| 20 | CH₃(CH₂)₂— | —NH | Oily |

| Example | IR $\nu_{cm^{-1}}^{max}$ | NMR δppm (CDCl₃) |
|---|---|---|
| 1 | 1740, 1640, 1590, 1500, 1420 (neat) | 2.65–2.70(m, 2H), 3.04–3.10(m, 2H), 3.41–3.65(m, 8H) 7.24–7.39(m, 5H), 8.29–8.32(m, 2H), 8.76–8.78(m, 2H) 9.24(s, 2H) |
| 2 | 1740, 1720, 1640, 1600, 1510, 1450 (KBr) | 2.57–2.69(m, 2H), 2.98–3.08(m, 2H), 3.40–3.64(m, 8H) 7.18–7.56(m, 9H), 8.03–8.06(m, 4H) |
| 3 | 1750, 1640, 1500, 1480 (neat) | 1.33(s, 18H), 2.55–2.63(m, 2H), 2.89–3.00(m, 2H) 3.21–3.34(m, 2H), 3.44–3.65(m, 6H), 6.90–7.10(m, 3H) |
| 4 | 1760, 1630, 1500, 1460, 1430 (neat) | 1.01–1.07(m, 6H), 1.69–1.83(m, 4H), 2.42–2.54(m, 6H) 2.87–2.96(m, 2H), 3.01–3.31(m, 2H), 3.40–3.48(m, 6H) 6.96–7.08(m, 3H) |
| 5 | 3280, 2940, 1740, 1630, 1590, 1555, 1420, 1260, 1190 (KBr) | 0.91(t, 3H), 1.25–1.66(m, 4H), 2.48(t, 2H), 3.02–3.26(m, 4H), 7.20–7.38(m, 5H), 8.27–8.32(m, 2H) 8.75–8.78(m, 2H), 9.22–9.23(m, 2H) |
| 6 | 3260, 2920, 1740, 1630, 1560, 1260, 1200, 1110 | 0.90(t, 3H), 1.22–1.48(m, 4H), 2.46(t, 2H), 3.02(t, 2H), |

TABLE 1-continued

Compound of the present invention

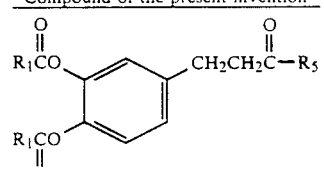

| | | |
|---|---|---|
| | (KBr) | 3.14–3.24(m, 2H), 5.50(brs, 1H), 7.14–7.55(m, 9H), 8.00–8.04(m, 4H) |
| 7 | 3300, 2960, 1760, 1640, 1540, 1505, 1480, 1255, 1200, 1120 (neat) | 0.89(t, 3H), 1.21–1.73(m, 22H), 2.41(t, 2H), 2.94(t, 2H), 3.14–3.21(m, 2H), 5.35(brs, 1H), 6.93–7.06(m, 3H) |
| 8 | 3280, 2960, 1760, 1640, 1500, 1255, 1140, 1010 (neat) | 0.86–0.92(m, 3H), 1.01–1.07(m, 6H), 1.23–1.45(m, 4H), 1.69–1.83(m, 4H), 2.37–2.52(m, 6H), 2.91–2.96(m, 2H), 3.13–3.21(m, 2H), 5.64(brs, 1H), 6.99–7.07(m, 3H) |
| 9 | 3400, 2920, 1710, 1640, 1530, 1430, 1260, 1120 (KBr) | 0.96–1.86(m, 10H), 2.39–2.45(m, 2H), 2.89–2.94(m, 2H), 3.62–3.80(m, 1H), 5.15–5.25(m, 1H), 6.91–7.46(m, 5H), 8.42–8.46 (m, 2H), 8.81–8.84 (m, 2H), 9.39–9.41(m, 2H) |
| 10 | 3280, 2920, 1740, 1630, 1550, 1255, 1110 (KBr) | 0.98–1.88(m, 10H), 2.46(t, 2H), 3.02(t, 2H), 3.70–3.75 (m, 1H), 5.22–5.25(m, 1H), 7.15–7.56(m, 9H), 8.06(m, 4H) |
| 11 | 3280, 2920, 1760, 1640, 1540, 1505, 1480, 1255, 1200, 1120 (neat) | 0.96–1.87(m, 28H), 2.39(t, 2H), 2.94(t, 2H)3.65–3.80 (m, 1H), 5.26–5.29(m, 1H), 6.94–7.07(m, 3H) |
| 12 | 3280, 2920, 1740, 1630, 1540, 1240, 1140 (KBr) | 0.95–1.41(m, 10H), 1.57–1.83(m, 10H), 2.36–2.57(m, 6H), 2.91–3.00(m, 2H), 3.64–3.76(m, 1H), 5.18–5.20(m, 1H), 7.00–7.05(m, 3H) |
| 13 | 2860, 1740, 1630, 1500, 1440, 1420, 1020 (neat) | 1.80–2.00(m, 4H), 2.60–2.70(m, 2H), 3.00–3.10(m, 2H), 3.30–3.50(m, 4H), 7.20–7.40(m, 5H), 8.30–8.40(m, 2H)8.80–8.90 (m, 2H), 9.20–9.30(m, 2H) |
| 14 | 1740, 1630, 1500, 1450, 1250, 1110, 700 (KBr) | 1.80–2.00(m, 4H), 2.60–2.80(m, 2H), 3.00–3.10(m, 2H), 3.30–3.50(m, 4H), 7.20–7.60(m, 9H), 8.00–8.20(m, 4H) |
| 15 | 2860, 1750, 1640, 1250, 1120, 1030, 890, 750 (neat) | 1.33(s, 18H), 1.80–2.00(m, 4H), 2.50–2.60(m, 2H), 2.90–3.00(m, 2H), 3.20–3.50(m, 4H), 6.90–7.10(m, 3H) |
| 16 | 2860, 1760, 1620, 1440, 1250, 1190, 1110 (KBr) | 1.00–1.10(m, 6H), 1.70–2.00(m, 8H), 2.40–2.60(m, 6H), 2.90–3.00(m, 2H), 3.20–3.30(m, 2H), 3.40–3.50(m, 2H), 6.90–7.10(m, 3H) |
| 17 | 2900, 1740, 1500, 1190, 1110, 1020, 720 (KBr) | 1.60–2.20(m, 15H), 2.40–2.50(m, 2H), 2.90–3.00 (m, 2H), 5.23(s, 1H), 7.10–7.50(m, 5H), 8.20–8.30(m, 2H), 8.70–8.80(m, 2H), 9.20–9.30(m, 2H) |
| 18 | 2900, 1740, 1450, 1110, 1060, 700 (KBr) | 1.61–2.10(m, 15H), 2.30–2.40(m, 2H), 2.90–3.00 (m, 2H), 5.10(s, 1H), 7.10–7.50(m, 9H), 8.00–8.10(m, 4H) |
| 19 | 2900, 1760, 1640, 1480, 1250, 1120, 1030, 890 (KBr) | 1.33(s, 18H), 1.60–2.10(m, 15H), 2.30–2.40(m, 2H), 2.80–2.90(m, 2H), 5.20(s, 1H), 6.90–7.10(m, 3H) |
| 20 | 3300, 1760, 1640, 1450, 1360, 1250, 920 (neat) | 1.00–1.10(m, 6H), 1.60–2.10(m, 19H), 2.20–2.50 (m, 6H), 2.80–2.90(m, 2H), 5.05 (m, 1H)6.90–7.10(m, 3H) |

EXAMPLE 21

Promotional Function of NGF Production and Secretion to L·M Cells of a Mouse

This experiment was made in accordance with Furukawa et al.'s method [Y. Furukawa et al., J. Biol. Chem., 261, 6039–6047 (1986)].

That is, L·M cells were precultured in Culture Medium 199 (made by Gibco Co., Ltd.) containing 0.5% peptone, and the cells were planted in a 24-hole culture plate (made by Falcon Co., Ltd., a culture area per culture hole=2.1 cm$^2$) in a ratio of about $3 \times 10^4$ cells/culture hole. Afterward, they were cultured at 37° C. for 3 days so as to be a complete confluent (about $10^6$ cells/culture hole). The culture medium was then replaced with Culture Medium 199 (0.5 ml/culture hole) containing 0.5% bovine serum albumin (the fifth section, made by Armour Co., Ltd.). A compound to be tested was contained at a predetermined concentration in this culture medium, and after 24 hours, the concentration of NGF in the culture medium was measured by a highly sensitive ELISA method [S. Furukawa et al., J. Neruochem., 40, 734–744 (1983)].

The results were each shown by a magnification of the concentration of NGF in a culture medium for a control in which the compound to be tested was not contained. The detection limit of the ELISA method was 0.25 pg/ml, and the NGF concentration of the control was usually from 50 to 200 pg/0.5 ml of the culture hole. Each value of the results is an average of four pilots in which the same cell preparation was used. The results are set forth in Table 2.

EXAMPLE 22

Promotional Function of NGF Production and Secretion to Astroglia Cells of a Mouse Brain Astroglia cells were derived from a mouse forebrain, and then transferred to a culture medium [S. Furukawa et al., Biochem. Biophys. Res. Commun., 136, 57–63 (1986)].

That is, the brain of a eight-day-old mouse was thinly sliced and then washed with a phosphoric acid buffering physiological saline solution (hereinafter abbreviated as "PBS") not containing calcium and magnesium. Afterward, the brain slices were treated at 37° C. for 30 minutes in PBS containing 0.25% of trypsin, and the brain tissue was then scattered sufficiently by the use of a Pasteur pipet so as to form a suspension. The latter was then centrifuged at $200 \times g$ for 5 minutes to recover the cells and cell aggregates. They were transferred to a Darbekko-modified Eagle's culture medium (hereinafter abbreviated as "DMEM culture medium", made by Gibco Co., Ltd.) containing 10% of fetal bovine serum, $5 \times 10^5$ unit ml of penicillin and 5 μg/ml of streptomycin, and primary culture was carried out for a period of from 10 to 14 days, with the same kind of culture medium being renewed every 3 days. After confluent had been reached, the cells were treated with trypsin, and they were distributed and then replanted in another culture medium. Furthermore, the replanting was repeated twice or more in order to obtain a morphologically uniform cell population. In this experiment, there is used a PAP staining method (peroxidase antiperoxidase staining method) using an antihuman glia fiber protein (GFAP) rabbit antiserum, and the above-mentioned cell population was stained as much as 97% or more. This cell population would be called astroglia cells.

The astroglia cells were planted in a 24-hole culture plate (made by Falcon Co., Ltd., a culture area per culture hole=2.1 cm$^2$) in a ratio of about $3 \times 10^4$ cells/culture hole. Afterward, they were cultured for 3 days in a DMEM culture medium containing a 10% fetal bovine serum so as to be a complete confluent (about $10^7$ cells/culture hole). The culture medium was replaced with a DMEM culture medium containing 0.5% bovine serum albumin (the fifth section) (0.5 ml/culture hole), and the astroglia cells were then cultured for 3 days. Furthermore, this kind of culture medium was renewed every 3 days in order to lead the cells to a quiscent stage. Afterward, the culture medium was replaced with 0.5 ml of the similar culture medium containing a compound to be tested at a predetermined concentration, and after 24 hours, the concentration of NGF in the culture medium was measured by a highly sensitive ELISA method. The results were each obtained as a magnification of the NGF concentration in a culture medium for a control in which the compound to be tested was not contained. The detection limit of the ELISA method as 0.25 pg/ml, and the NGF concentration of the control was usually form 1 to 10 pg/0.5 ml of the culture hole. Each value of the results is an average of four pilots in which the same cell preparation was used. The results are set forth in Table 3.

TABLE 2

(promotional function of NGF production and secretion to mouse L · M cells)

| Compound (Example No.) | Concentration of Sample (mM) | Concentration of NGF (ng/well) | Increase of NGF (magnification to control) |
|---|---|---|---|
| Control | 0 | 0.34 | 1.00 |
| 1 | 0.4 | 1.36 | 4.00 |
| 2 | 0.4 | 1.22 | 3.59 |
| 3 | 0.4 | 1.30 | 3.82 |
| 4 | 0.4 | 1.45 | 4.26 |
| 5 | 0.2 | 2.10 | 6.18 |
| 6 | 0.2 | 2.02 | 5.94 |
| 7 | 0.2 | 1.88 | 5.53 |
| 8 | 0.2 | 2.18 | 6.41 |
| 9 | 0.4 | 1.20 | 3.53 |
| 10 | 0.4 | 1.63 | 4.79 |
| 11 | 0.4 | 1.33 | 3.91 |
| 12 | 0.4 | 1.38 | 4.06 |
| 13 | 0.2 | 2.00 | 5.88 |
| 14 | 0.2 | 2.01 | 5.91 |
| 15 | 0.2 | 1.97 | 5.79 |
| 16 | 0.2 | 2.20 | 6.47 |
| 17 | 0.4 | 2.03 | 5.97 |
| 18 | 0.4 | 2.04 | 6.00 |
| 19 | 0.4 | 1.96 | 5.76 |
| 20 | 0.4 | 1.93 | 5.68 |

TABLE 3

(promotional function of NGF production and secretion to astroglia cells of mouse brain)

| Compound (Example No.) | Concentration of Sample (mM) | Concentration of NGF (ng/well) | Increase of NGF (magnification to control) |
|---|---|---|---|
| Control | 0 | 40.5 | 1.00 |
| 1 | 0.4 | 208.2 | 5.14 |
| 2 | 0.4 | 199.4 | 4.92 |
| 3 | 0.4 | 218.6 | 5.40 |
| 4 | 0.4 | 222.7 | 5.50 |
| 5 | 0.2 | 380.2 | 9.39 |
| 6 | 0.2 | 370.5 | 9.15 |
| 7 | 0.2 | 363.8 | 8.98 |
| 8 | 0.2 | 387.4 | 9.57 |
| 9 | 0.4 | 206.1 | 5.09 |
| 10 | 0.4 | 200.8 | 4.96 |
| 11 | 0.4 | 197.6 | 4.88 |
| 12 | 0.4 | 190.4 | 4.70 |
| 13 | 0.2 | 330.5 | 8.16 |
| 14 | 0.2 | 375.5 | 9.27 |
| 15 | 0.2 | 380.4 | 9.39 |
| 16 | 0.2 | 282.6 | 6.98 |
| 17 | 0.2 | 373.2 | 9.21 |
| 18 | 0.2 | 369.7 | 9.13 |
| 19 | 0.2 | 381.0 | 9.41 |
| 20 | 0.2 | 390.6 | 9.64 |

What is claimed is:

1. A dihydrocaffeic acid derivative represented by the formula (I)

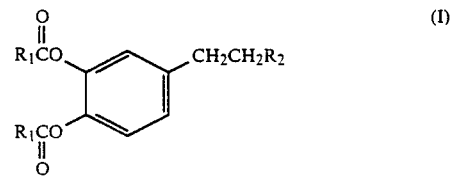

wherein $R_1$ is an alkyl group having 2 or more carbon atoms, an aryl group, a phenethyl group, p-methylphenyl group, a benzyl group, a pyridyl group, pyrimidyl group, imidazolyl group, or furyl group; $R_2$ is

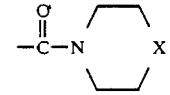

and X is an oxygen atom or a salt of said derivative.

2. The compound according to claim 1 wherein $R_1$ is a phenyl group.

3. The compound according to claim 1 wherein $R_1$ is a pyridyl group.

4. The compound according to claim 1 wherein $R_1$ is a t-butyl group.

5. The compound according to claim 1 wherein $R_1$ is a propyl group.

6. The compound according to claim 1 wherein $R_2$ is

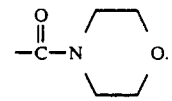

7. A pharmaceutical composition for inhibiting or treating regressive disorders of the central nervous system which contains together with a pharmaceutically acceptable carrier a dihydrocaffeic acid derivative represented by formula (I) of claim 1 and its salt as effective ingredients.

* * * * *